United States Patent [19]

Davies

[11] Patent Number: 4,672,961
[45] Date of Patent: Jun. 16, 1987

[54] RETROLASING CATHETER AND METHOD

[76] Inventor: David H. Davies, 4964 Sundance Sq., Boulder, Colo. 80301

[21] Appl. No.: 865,073

[22] Filed: May 19, 1986

[51] Int. Cl.⁴ ............................................. A61B 17/36
[52] U.S. Cl. ................................. 128/303.1; 128/398
[58] Field of Search ...................... 128/303.1, 395–398

[56] References Cited

U.S. PATENT DOCUMENTS

| | | | |
|---|---|---|---|
| 1,791,794 | 2/1931 | Chesney | 128/398 |
| 4,072,147 | 2/1978 | Hett | 128/303.1 |
| 4,207,874 | 6/1980 | Choy | 128/6 |
| 4,445,892 | 5/1984 | Hussein et al. | 128/303.1 X |
| 4,512,762 | 4/1985 | Spears | 128/398 |
| 4,539,987 | 9/1985 | Nath | 128/398 X |
| 4,576,177 | 3/1986 | Webster, Jr. | 128/660 |

FOREIGN PATENT DOCUMENTS 0153847 2/1985 European Pat. Off. .

Primary Examiner—Lee S. Cohen
Attorney, Agent, or Firm—Fields, Lewis, Pittenger & Rost

[57] ABSTRACT

An apparatus and method for retrolasing plaque deposits in a coronary artery to remove same includes a tip assembly on the end of a flexible inner tube containing optical fibers that are slidable along a guide wire. The tip assembly includes a reflective surface rearwardly of a front face that directs laser energy supplied through the optical fibers in a rearward direction through a window portion to a focal point externally of the tip assembly. The deposit is removed as the tip assembly is moved in a rearward progression back through the deposit.

13 Claims, 6 Drawing Figures

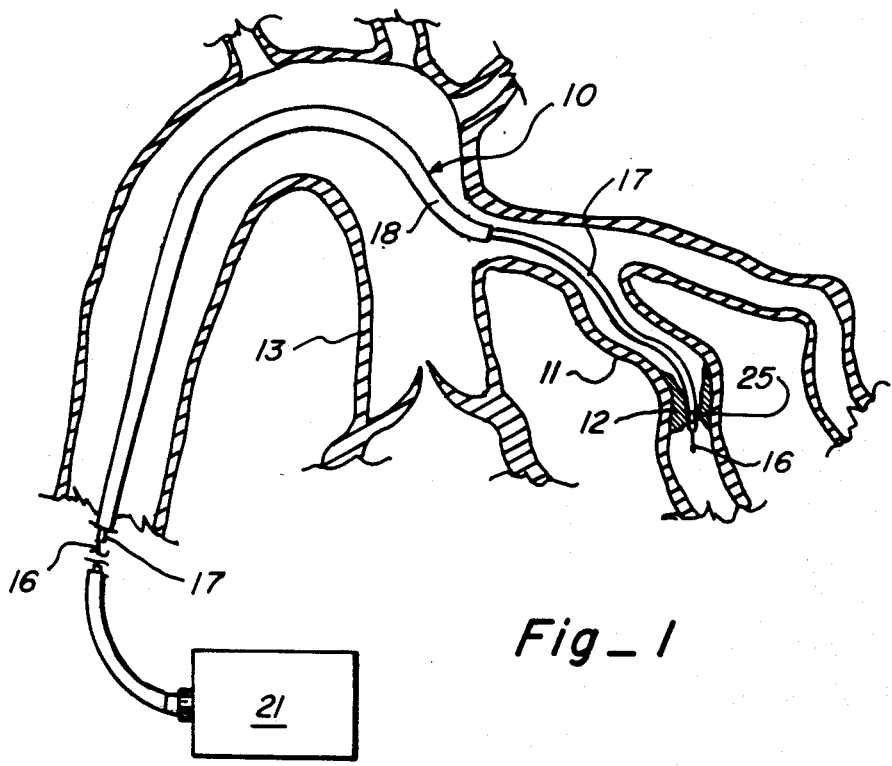
Fig_1
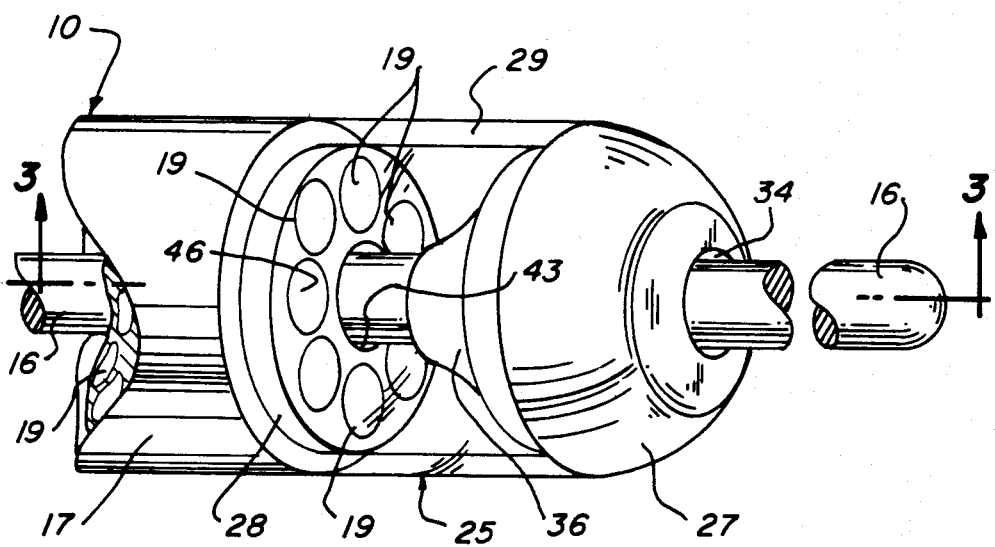
Fig_2

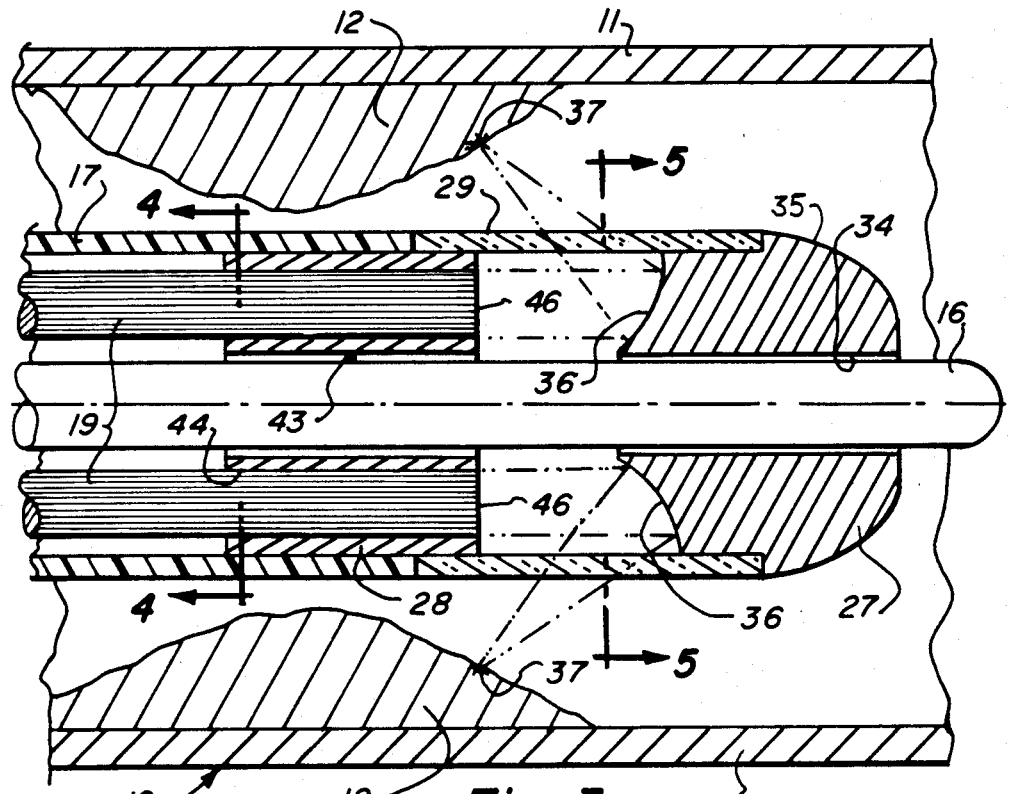
Fig_3
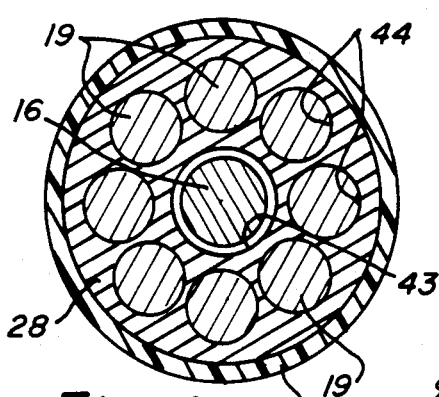
Fig_4
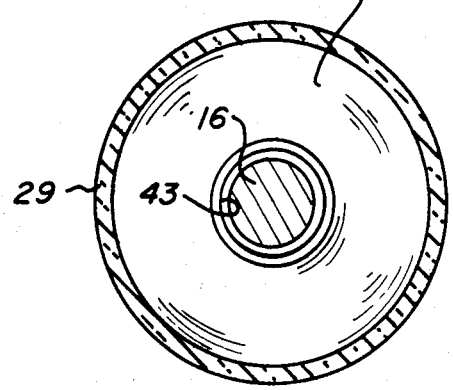
Fig_5
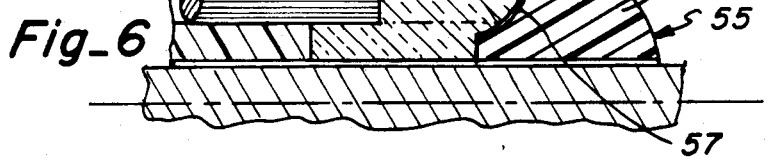
Fig_6

4,672,961

RETROLASING CATHETER AND METHOD

TECHNICAL FIELD

This invention relates generally to recanalizing blood vessels and more particularly to a novel and improved apparatus and method for removing plaque deposits from diseased arteries.

BACKGROUND ART

Surgical by-pass procedures and balloon angioplasty are two techniques currently available for recanalizing arteries. The techniques of balloon angioplasty involve the passage of a fine guide-wire through the narrowed area, and the advancing of a catheter carrying the balloon through the narrowed area, so that the balloon rests in the narrowed area or site of stenosis. The balloon is then inflated.

In recent years much attention has been given to the use of laser energy for angioplasty. It has been demonstrated that laser energy can be effective in removing atherosclerotic plaque deposits and much research is currently being done to establish effective techniques. Clinical application has been seriously limited, especially in the coronary circulation, by the risk of perforation of the artery. To date the catheter is inserted and the laser energy is directed forward (antegrade lasing) so that in a tortuous artery it is difficult precisely to direct the energy against the deposit. Thus a perforation can be induced, which of course could be lethal.

Representative balloon angioplasty devices and methods using antegrade lasing are disclosed in the U.S. Pat. Nos. 4,207,874, 4,512,762, 4,576,177, and European patent application no. 153,647.

DISCLOSURE OF INVENTION

An apparatus and method for directing laser energy in a coronary artery to remove plaque deposits is disclosed. A tip assembly on the end of a flexible tube containing optical fibers is movable along a guide wire through the artery. The tip assembly has a backwardly facing laser energy reflecting surface, preferably a segment of a parabola, that rearwardly directs and focuses laser energy delivered thereto by the optical fibers on focal points externally to the catheter to remove plaque deposits during a rearward progression of the tip assembly back through the deposit. One form has a front head portion in which the surface is cut and polished. Another form has a reflective coating on the forward curvilinear end of a window body portion that passes laser energy.

BRIEF DESCRIPTION OF THE DRAWINGS

FIG. 1 is a schematic diagram showing a retrolasing catheter in place in a coronary artery.

FIG. 2 is a perspective view of one form of tip assembly of the retrolasing catheter.

FIG. 3 is a sectional view taken along lines 3—3 of FIG. 2.

FIG. 4 is a sectional view taken along lines 4—4 of FIG. 3.

FIG. 5 is a sectional view taken along lines 5—5 of FIG. 3.

FIG. 6 is a fragmentary sectional view showing an alternative form of tip assembly.

DETAILED DESCRIPTION

Referring now to the drawings there is shown in FIG. 1 a retrolasing catheter 10 embodying features of the present invention in a coronary artery 11. In particular the artery illustrated is the left anterior descending artery which has what is commonly referred to as a plaque deposit 12 which narrows the artery. The catheter 10 is shown as extending through the aorta 13 and into the artery 11 as is conventional practice in balloon angioplasty.

The catheter 10 shown is comprised of an inner guide wire 16 of a length that will extend through the artery and pass through the deposit 12, a flexible inner tube 17 telescoping over and slidable along the guide wire and a flexible guiding tube 18 that telescopes over a portion of inner tube 17 and extends as far as the entrance to artery 11. There is further provided within tube 17 a plurality of circumferentially spaced optical fibers 19 that extend from a source of laser energy 21 located externally of the patient's body to the distal end of the inner tube 17 which conduct laser energy therethrough.

A tip assembly 25 is provided at the distal end of the inner tube 17 which in general includes a front head portion 27, an intermediate tubular portion 29 arranged along a common longitudinal axis and a rear template portion 28.

The front head portion 28 has a central bore 34 through which guide wire 16 extends, a rounded nose or front face 35 to facilitate its being pushed through the artery with a minimum of resistance and a rearwardly diverging rear face 36. The rear face 36 has a curvilinear shape, preferably a segment of a parabola, with a focus or focal point 37 a selected distance beyond the external peripheral surface of the tip assembly. The axis of the parabola is arranged parallel to the longitudinal axis of the tip assembly and the optical fibers are arranged along and parallel to the longitudinal axis of the assembly so that the laser energy passing from the end surface 46 will strike the surface and pass through the focal point of the parabolic surface 36. Since the assembly is tubular in form the parabolic surface extends around the longitudinal axis of the assembly a full 360° to remove the deposits.

The rear face 36 is a mirror or reflective surface that will reflect laser energy. In this form the head portion 27 is preferably made of silver with the rear face machined therein and polished to provide the reflective surface.

The template portion 28 has a central bore 43 extending along the longitudinal axis of the assembly through which the guide wire extends and a plurality of circumferentially spaced positioning bores 44 arranged parallel to the longitudinal axis through which an optical fiber extends. Thus the template portion functions to precisely position the ends of the fibers in relation to the reflective surface. The fiber ends are spaced a selected distance from the longitudinal axis and are equally spaced from one another to provide a balanced array. The distal end 46 of each optical fiber 19 is cut at right angles to the axis of the fiber and each terminates in a common plane along the front face of the template portion and directs laser energy against rearwardly facing reflective face 36 from which it is focused on focal point 37 a selected distance externally of the tip assembly 25.

The intermediate tubular portion 29 is translucent to laser energy and preferably is made of sapphire to form a window capable of passing laser energy therethrough.

Referring now to FIG. 6 there is shown an alternative tip assembly 55 wherein a tubular body 56 translucent to laser energy, preferably sapphire, is provided. This tubular body forms a window for the laser energy and is solid between the ends 46 of the optical fibers 19 and template portion 28 and a curvilinear front end surface. The front end surface of body 56 is coated with a coating 57 of silver or the like to provide a reflective surface 58 to direct the laser energy to focal points 59 around the external peripheral surface of the tip assembly. In this form a rounded front nose 61 forwardly of the coating of plastic or the like facilitates movement of the tip assembly 55 through the artery.

A pulsed excimer operating in the ultraviolet range has been found to provide satisfactory results for the source of laser energy 21. For instance, ablation of calcified plaque is probably most efficiently carried out in the ultraviolet range rather than the visible spectrum. A suitable example is light energy having a 308 nm wavelength, 70 ns pulse duration, giving 111mJ/mm$^2$. The optical fibers appear to sustain this without damage. Pulses having a 40 ns duration have also been found satisfactory.

By way of example and not limitation the following dimensions would be suitable for the above described device:

length of tip assembly 25 2.5 mm
diameter of tip assembly 25 1-1.5 mm
distance of focal point from surface of tip assembly 25 ½-1 mm
diameter of guide wire 16 0.33 mm
diameter of optical fiber 19 0.33 mm In use, the catheter 10 is inserted into the artery 11 so that the guide wire 16 passes through the deposit 12. The inner catheter tube 17 and tip assembly 25 is slipped over the guide wire and advanced until the tip assembly has passed the deposit 12. The laser energy is transmitted from source 21 through the optical fibers and is reflected back from surface 36 to the focal points 37 of the reflective surface as the tip assembly is retracted to remove the deposit. In this way the directing of the energy against the deposit can be carefully controlled to avoid perforating the artery.

Although the present invention has been described with a certain degree of particularity, it is understood that the present disclosure has been made by way of example and that changes in details of structure may be made without departing from the spirit thereof.

What is claimed is:

1. In a catheter adapted to be inserted into a coronary artery and the like for removing plaque deposits which narrow the artery including at least an inner guide wire, a flexible tube having a distal end slidable over said guide wire, and optical fibers having distal ends extending through said tube to transmit laser energy from a source to said distal end of said tube, the combination comprising:
a tip assembly on the distal end of said tube having a central bore portion through which the guide wire extends for guided movement through the artery, said assembly having a window portion, an external surface and a backwardly facing laser energy reflective surface for reflecting laser energy delivered through the distal ends of said optical fibers in a forward direction along the longitudinal axis of said assembly in a reversed direction back through said window portion and focusing said laser energy at focal points of said reflective surface a selected distance beyond the external surface of said assembly.

2. In a catheter as set forth in claim 1 wherein said tip assembly includes a front head portion having a rounded front face and a rearwardly diverging rear face of curvilinear shape.

3. In a catheter as set forth in claim 2 wherein said head portion is made of silver and said rear face is polished to reflect said laser energy.

4. In a catheter as set forth in claim 2 wherein said head portion has a tubular body translucent to laser energy with a curvilinear front end surface provided with a reflective coating to form said reflective surface and a rounded front face.

5. In a catheter as set forth in claim 1 wherein said window portion is made of sapphire.

6. In a catheter as set forth in claim 1 wherein said laser energy reflective surface is a segment of a parabola which extends around the longitudinal axis of the assembly a full 360 degrees.

7. In a retrolasing catheter as set forth in claim 1 wherein the distal ends of said fibers are in planes at right angles to said longitudinal axis of said assembly and are in a common plane.

8. In a retrolasing catheter adapted to be inserted into a coronary artery and the like for removing plaque deposits which narrow said artery including an inner guide wire, a flexible inner tube having a distal end slidable over said guide wire and optical fibers having distal ends extending through said inner tube, the combination comprising:
a tip assembly on the distal end of said inner tube including a front head portion, intermediate window portion, and a rear template portion, said assembly having an external surface and a rearwardly facing laser energy reflecting surface having a shape which is a segment of a parabola disposed rearwardly of said front head portion for reflecting back laser energy delivered in a forward direction through the distal ends of said optical fibers along the longitudinal axis of said assembly in a reversed direction back through said window portion and focusing said laser energy at focal points of said reflecting surface a selected distance beyond the external surface of said assembly for removing plaque deposits as said assembly is pulled back through said deposits, said rear template portion having a central bore through which said guide wire extends and a plurality of circumferentially spaced positioning bores spaced radially out from said central bore by which said optical fibers are positioned along the longitudinal axis of said assembly with the axis of said fibers being parallel to the axis of said parabola to direct laser energy toward said reflective surface.

9. In a retrolasing catheter adapted to be inserted into a coronary artery and the like for removing plaque deposits which narrow said artery including an inner guide wire, a flexible inner tube having a distal end slidable over said guide wire, a flexible guiding tube over said inner tube and optical fibers having distal ends extending through said inner tube, the combination comprising:
a tip assembly on the distal end of said inner tube including a front head portion, intermediate window portion, and a rear template portion, said front head portion having a rounded front face, said assembly having an external surface and a rearwardly facing laser energy reflecting surface having a curvilinear shape which is a segment of a parabola disposed rearwardly of said front head portion for reflecting back laser energy delivered in a forward direction through the distal ends of said optical fibers along the longitudinal axis of said assembly in a reversed direction back through said window portion and focusing said laser energy at focal points of said reflecting surface a selected distance beyond the external surface of said assembly for removing plaque deposits as said assembly is pulled back through said deposits, said rear template portion having a central bore through which said guide wire extends and a plurality of circumferentially spaced positioning bores spaced radially out from said central bore by which said optical fibers are positioned along the longitudinal axis of said assembly with the axis of said fibers being parallel to the axis of said parabola to direct laser energy toward said reflective surface.

10. A method of removing plaque deposits in a coronary artery and the like comprising the steps of:
    inserting a catheter including a tip assembly at an end of a flexible tube carrying optical fibers arranged to slide over a guide wire into a coronary artery narrowed by a plaque deposit and
    deflecting laser energy delivered to and through said optical fibers to said tip assembly in a backward direction from said tip assembly and to a focal point externally of said tip assembly in a plaque deposit as the tip assembly is being withdrawn from the artery to remove said deposit.

11. In a catheter adapted to be inserted into a coronary artery and the like for removing plaque deposits which narrow the artery including a flexible tube having a distal end and at least one optical fiber having a distal end extending through said tube to transmit laser energy from a source to said distal end of said tube, the combination comprising:
    a tip assembly on the distal end of said tube, said assembly having a window portion, an external surface and a backwardly facing laser energy reflective surface for reflecting laser energy delivered through the distal end of said optical fiber in a forward direction along the longitudinal axis of said assembly in a reversed direction back through said winidow portion and focusing said laser energy at foacl points of said reflective surface a selected distance beyond the external surface of said assembly.

12. A method of removing plaque deposits in a coronary artery and the like comprising the steps of:
    inserting a catheter including a tip assembly at an end of a flexible tube carrying at least one optical fiber into a coronary artery narrowed by a plaque deposit and
    deflecting laser energy delivered to and through said optical fiber to said tip assembly in a backward direction from said tip assembly and to a focal point externally of said tip assembly in a plaque deposit to remove said deposit.

13. In a catheter adapted to be inserted into a coronary artery and the like for removing plaque deposits which narrow the artery including at least an inner guide wire, a flexible tube having a distal end slidable over said guide wire, and optical fibers having distal ends extending through said tube to transmit laser energy from a source to said distal end of said tube, the combination comprising:
    a tip assembly on the distal end of said tube having a central bore portion through which the guide wire extends for guided movement through the artery, said assembly having a window portion, an external surface and a backwardly facing laser energy reflective surface for reflecting laser energy delivered through the distal ends of said optical fibers in a forward direction along the longitudinal axis of said assembly in a reversed direction back through said window portion and focusing said laser energy at focal points of said reflecting surface a selected distance beyond the external surface of said assembly,
    said laser energy reflective surface being a segment of a parabola which extends around the longitudinal axis of the assembly a full 360 degrees, and
    said tip assembly having a rear template portion with a central bore through which the guide wire extends and a plurality of circumferentially spaced positioning bores spaced radially out from said central bore through which said optical fibers extend and are positioned with their longitudinal axes parallel to the axis of the parabola to direct laser energy along the longitudinal axis of said assembly toward said reflective surface.

* * * * *